US011826551B2

(12) United States Patent
Atterbury et al.

(10) Patent No.: US 11,826,551 B2
(45) Date of Patent: Nov. 28, 2023

(54) AUTOINJECTORS HAVING ADVANCED RELEASE AND SOUND FEATURES

(71) Applicant: Battelle Memorial Institute, Columbus, OH (US)

(72) Inventors: William G. Atterbury, Columbus, OH (US); Steve Madland, Columbus, OH (US); Adam Fox, Columbus, OH (US); Steven E. Huckaby, Blacklick, OH (US); Jake Pyzza, Delaware, OH (US)

(73) Assignee: Battelle Memorial Institute, Columbus, OH (US)

( * ) Notice: Subject to any disclaimer, the term of this patent is extended or adjusted under 35 U.S.C. 154(b) by 177 days.

(21) Appl. No.: 16/844,858

(22) Filed: Apr. 9, 2020

(65) Prior Publication Data

US 2020/0324051 A1 Oct. 15, 2020

Related U.S. Application Data

(60) Provisional application No. 62/831,658, filed on Apr. 9, 2019.

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157* (2013.01); *A61M 5/3202* (2013.01); *A61M 5/326* (2013.01); *A61M 2205/581* (2013.01); *A61M 2205/582* (2013.01)

(58) Field of Classification Search
CPC ................ A61M 5/2033; A61M 5/326; A61M 2005/3263; A61M 2205/58; A61M 2205/581; A61M 2205/582; A61M 5/24; A61M 5/31525; A61M 5/31528; A61M 5/31501; A61M 5/3269; A61M 5/3271; A61M 5/31585; A61M 2005/2013; A61M 2005/208
USPC ......................................................... 604/506
See application file for complete search history.

(56) References Cited

U.S. PATENT DOCUMENTS

| 8,062,255 | B2 | 11/2011 | Brunnberg |
| 9,017,293 | B2 | 4/2015 | Edhouse |
| 9,675,754 | B2 | 6/2017 | DeSalvo et al. |
| 9,895,492 | B2 | 2/2018 | Fabien et al. |
| 10,384,007 | B2 | 8/2019 | Henderson et al. |
| 10,384,016 | B2 | 8/2019 | Brereton et al. |
| 11,052,195 | B2 | 7/2021 | Atterbury |
| 2008/0177235 | A1* | 7/2008 | DiBiasi ................. A61M 5/326 604/192 |

(Continued)

OTHER PUBLICATIONS

International Preliminary Report on Patentability from International Application No. PCT/US2020/027499 dated Sep. 28, 2021.

(Continued)

*Primary Examiner* — Theodore J Stigell
*Assistant Examiner* — Nidah Hussain
(74) *Attorney, Agent, or Firm* — Frank Rosenberg; Susanne A. Wilson; Mui Tran (57) ABSTRACT

Autoinjectors and methods of injection are described that feature release mechanisms and/or end-of-dose sound which can operate in conjunction with a powered plunger to efficiently inject a controlled dose from a syringe.

9 Claims, 5 Drawing Sheets

(56) References Cited

U.S. PATENT DOCUMENTS

| | | | |
|---|---|---|---|
| 2015/0165130 A1* | 6/2015 | Butler | A61M 5/31543 604/211 |
| 2015/0335829 A1* | 11/2015 | Giambattista | A61M 5/3146 604/192 |
| 2017/0246395 A1 | 8/2017 | Daniel | |
| 2017/0354779 A1 | 12/2017 | Atterbury et al. | |
| 2019/0151557 A1* | 5/2019 | Senior | A61M 5/31536 |

OTHER PUBLICATIONS

International Search Report from International Application No. PCT/US2020/02749 dated Aug. 18, 2020.
Written Opinion from International Application No. PCT/US2020/027499 dated Aug. 18, 2020.
Lange et al., "Usability of a new disposable autoinjector platform device: results of a formative study conducted with a broad user population", Medical Devices: Evidence and Research, (2015) 8: 255-264, Ypsomed AG, Burgdorf, Switzerland.
SiIMPONI (golimumab) SmartJect autoinjector, "Instructions for Use", Janssen Biotech, Inc., Horsham, PA, 2015.
Pegasys Proclick Autoinjector, "Instructions for Use", Genentech, South San Francisco, CA, 2017.
TRULICITY (dulaglutide) Single-Dose Pen, "Instructions for Use", Eli Lilly, Indianapolis, IN, 2014.
Aranesp (darbepoetin alfa) Single-Use Prefilled SureClick™ Autoinjector, "Patient Instructions for Use", Amgen, Thousand Oaks, CA, 2001.

* cited by examiner

AUTOINJECTORS HAVING ADVANCED RELEASE AND SOUND FEATURES

RELATED APPLICATIONS

This application claims the priority benefit of U.S. Provisional Patent Application No. 62/831,658 filed Apr. 9, 2019.

INTRODUCTION

Protein therapeutics is a class of drug therapy that provides treatment for a broad range of diseases, such as autoimmune disorders, cardiovascular diseases, and cancer; however, delivery of protein therapeutics is often challenging because of the high viscosity and the high forces needed to push viscous formulations through a parenteral device. An autoinjector suitable for injecting a viscous composition needs to be able to apply enough force to comfortably insert a needle into the skin of a patient and to push viscous and/or higher volume doses of fluid medication out of a syringe into the patient. Another challenge is that the typical autoinjector activates by pushing a button. However, many patients, due to disease or other circumstances, may lack the ability needed to correctly place the autoinjector at the appropriate injection site and press a button on the distal end of the device to activate the device. In addition, many autoinjectors lack a way to provide feedback to the patient that medication delivery is complete and that the device may be removed from the injection site. Without such feedback to the patient, the full dose of medication may not be delivered during an injection due to early removal from the injection site.

Because of the importance of parenteral delivery of proteins, extensive efforts have been expended on developing improved autoinjectors. These efforts have included methods and internal devices that create audible or tactile feedback to the patient at various points of injection. For example, Atterbury et al. in U.S. Published Patent Application No. 2017/0354779 describe an autoinjector with a number of sound elements that engage during injection with the intent of providing feedback on progression of the injection stroke. Fabien et al. in U.S. Pat. No. 9,895,492 describe an autoinjector that has an actuation sleeve and can include a separate sound device to provide an indication of end of dose. DeSalvo et al. in U.S. Pat. No. 9,675,754 describe an autoinjector that is powered by liquified gas. Features of the power apparatus can be modified to produce sound at prescribed times and to provide a lock out feature. Brereton et al. in U.S. Pat. No. 10,384,016 describe an autoinjector that is powered by a spring that is released with a button; additional sound elements are required to produce audible and tactile feedback.

Other autoinjectors, such as the Pegasus ProClick, the Simponi Smartject, the SureClick™, and the TRULICITY autoinjector, have incorporated a click sound at the start and/or end of injection. Despite these and other efforts, there remains a need to develop injection methods and autoinjectors that increases patient compliance with improved characteristics such as simpler activation, better feedback mechanisms, and softer needle insertion in a device that will reliably deliver full doses of medication.

SUMMARY OF THE INVENTION

In a first aspect, the invention provides a method of releasing a mechanism for an injector (initiating plunger action—which would dispense a load held within the barrel of a syringe), comprising: pressing an activation sleeve that is located at a proximal end of an injector; wherein the activation sleeve rotates a locking collar using a camming action; wherein the rotation of the locking collar rotates a nut thereby releasing the autoinjector mechanism. In practice (and in the figures) the nut is in the form of nut sectors retained by a nut cap which are necessary for a practical manufacture of the device.

The invention can be further characterized by one or any combination of the following features: wherein the locking collar is rotationally keyed to the nut sectors such that when the locking collar rotates, the nut sectors cause plunger screw pins to rotate off support ledges; wherein the plunger screw pins are forced down a helical thread by the drive spring thereby inserting the needle and delivering medicant to a patient; wherein the plunger screw is rotationally keyed to the end cap whereby the end cap is prevented from rotating by features attached to a housing (the housing is a cylindrical body that surrounds the injector); wherein the end cap is attached with a cap lock that secures the end cap to the housing; wherein the end cap is attached and retained to the housing by welding, bonding, snap fit, or interference fit; wherein the activation sleeve is extended by a sleeve spring when the device is removed from a patient's skin surface after delivery of medication is complete; wherein the locking collar rotates as the activation sleeve is fully extended thereby locking the activation sleeve in a fully extended position after use.

In another aspect, the invention provides an autoinjector comprising:

an activation sleeve which is rotationally keyed to a housing and is adapted to slide axially within the housing, a sleeve spring that applies an axial force between the housing and the activation sleeve; a locking collar that is secured axially and can rotate within the housing and is adapted to rotate as the activation sleeve is pushed or allowed to extend; nut sectors that are rotated by rotation of the locking collar and are captured axially between the locking collar and an end cap; a nut cap which secures the nut sectors and supports one end of the drive spring; and an end cap that engages with features on the housing and is locked to the housing with a cap lock. The end cap retains the other internal components within the housing. The plunger screw has plunger screw pins that rest on nut sector shelfs at the start of a helical thread.

The invention can be further characterized by one or any combination of the following features: further comprising a plunger screw with plunger screw pins that rests on nut sector shelfs and is rotationally keyed to the end cap, and provides a seat for a drive spring; wherein the activation sleeve is used to activate the device; wherein the activation sleeve is extended by a sleeve spring after use to cover the needle and preventing exposure of the needle; wherein the locking collar is rotatable by the activation sleeve using ramped surfaces 17 that interact with a cam feature 18 in the locking collar; wherein the activation sleeve is locked at the fullest extended position by the locking collar after use; wherein the locking collar has features 19 that interact with the activation sleeve to prevent the activation sleeve from moving axially after being extended to the fullest extended position after use; or further comprising nut sectors with stepped thread capable of producing an audible sound to provide audible feedback to the user at the end of dose.

In another aspect, the invention provides a method of protecting exposure to a needle on an injector after an injection, comprising: providing an injector wherein the injector comprises an activation sleeve that is located at a proximal end of an injector and wherein the activation sleeve comprises a sleeve spring; applying a force to the activation sleeve from the sleeve spring to extend the activation sleeve when the device is removed from the skin surface of a patient; and rotating the locking collar near the distal end (end away from the patient) of the activation sleeve extension causing locking tabs to interact with the activation sleeve causing the activation sleeve to lock in the extended position.

In a further aspect, the invention provides a method of producing an audible or tactile feedback in an injector, comprising: providing an injector comprising a drive spring adapted to provide force to move a plunger screw in the proximal direction; the plunger screw comprising a pin adapted to ride in a thread formed by a nut; wherein the thread of the nut comprises an interruption; wherein, during operation of the injector, when the plunger screw pin encounters the interruption there is a sudden and rapid movement that causes the audible or tactile feedback.

In another aspect, the invention provides an autoinjector configured to produce an audible or tactile feedback to a user, comprising: an injector comprising a drive spring adapted to provide force to move a plunger screw in the proximal direction; the plunger screw comprising a pin adapted to ride in a thread formed by a nut; wherein the thread of the nut comprises an interruption; configured such that, during operation of the injector, when the plunger screw pin encounters the interruption there is a sudden and rapid movement that causes the audible or tactile feedback. An interruption comprises a discontinuity or sharp change in the slope of the surface of the thread upon which the pin rides.

The method or autoinjector capable of producing an audible or tactile feedback can be further characterized by one or any combination of the following features: wherein the interruption comprises a change in slope (second derivative) toward the distal direction followed by an abrupt change in slope in the proximal direction ultimately returning to approximately the same slope as prior to the interruption (force can be measured as described below); wherein the plunger screw proceeds in the proximal direction at a first force and, in the vicinity of the interruption, force on the plunger screw increases by at least 2.5 N, or at least 5 N, or in the range of 2.5 to 10 N and then reduces to the first force or less over a distance in the proximal direction over a distance of 4 mm or less, 2 mm or less, or 1 mm or less (or in the range of 0.3 to 3 mm); wherein the reduction in force is 2.5 N, or at least 5 N, or in the range of 2.5 to 10 N as compared to the first force; wherein the force on the plunger screw is constant within 5 N for a distance of at least 10 mm, or at least 20 mm, or in the range of 10 to 200 mm, as the plunger screw proceeds in the proximal direction prior to the interruption; wherein the plunger screw proceeds in the proximal direction at a first force and, in the vicinity of the interruption, force on the plunger screw increases by at least 10% or at least 20% or at least 25% or in the range of 10 to 50%) and then reduces to the first force or less over a distance in the proximal direction over a distance of 4 mm or less, 2 mm or less, or 1 mm or less (or in the range of 0.3 to 3 mm); wherein the reduction in force is 2.5 N, or at least 5 N, or in the range of 2.5 to 10 N (alternatively, force on the plunger screw increases by at least 10% or at least 20% or in the range of 10 to 50%) as compared to the first force; and/or wherein the force on the plunger screw is constant within 5 N (or within 20% or within 10%) for a distance of at least 10 mm, or at least 20 mm, or in the range of 10 to 200 mm, as the plunger screw proceeds in the proximal direction prior to the interruption.

GLOSSARY

The proximal end is the end directed towards the patient.
The distal end is the end directed away from the patient.
A stroke encompasses the events between activating the device and completed injection of the fluid medication.

A torsion spring is an elastic object that stores mechanical energy when it is twisted. A preferred form of a torsion spring is a helical wire. A compression spring stores energy when compressed and then releases that energy when the spring is released, and is preferably in the form of a helical wire. An extension spring is an elastic material (typically a helical spring) that stores energy when extended and releases that energy when the spring is released.

A compression spring is defined as a spring that, in its first released state, can be compressed by at least 10% (preferably at least 50%) and again released to recover at least 95% (preferably at least 99%) of its length in the first released state. A torsion spring, according to the present invention, in its relaxed state can be twisted at least about 180° (half twist), more preferably at least one full twist, or in some embodiments at least one and one half full twists, or in some embodiments between a half and a one-and-one-half full twists, and then return to its initial position. A combination compression and torsion spring has the properties of both a compression spring and a torsion spring.

The "driving force" is the axial force along the vector from the distal end to the proximal end that expels the medicine from the syringe (typically a conventional cylindrical syringe); and, typically, also pushes the needle through the skin of the patient.

The "insertion force" is the force (in Newtons (N)) exerted on the plunger during needle insertion.

The "injection force" is the force (in Newtons (N)) exerted on the plunger during injection of the fluid medication.

Various aspects of the invention are described using the term "comprising;" however, in narrower embodiments, the invention may alternatively be described using the terms "consisting essentially of" or, more narrowly, "consisting of."

DETAILED DESCRIPTION OF PREFERRED EMBODIMENTS OF THE INVENTION

The features described in this invention include a sleeve activation feature, a needle lockout feature, and an end-of-dose (EOD) indicator that is audible and/or tactile. A preferred autoinjector for application of the inventive features is the constant force autoinjector (CFAI) as described in U.S. Published Application No. US 20180200442, which is incorporated by reference as if reproduced in full below. The preferred autoinjector comprises a combination compression and torsion spring that powers a plunger movement assembly (PMA) with a plunger screw, a syringe attached to the outer casing and/or a proximal end of the PMA, and a hollow needle attached to the proximal end of the syringe. Although a compression-torsion spring autoinjector such as shown in US 20180200442 is preferred, one or any combination of the inventive features may be applied to any autoinjector.

Figure 1:
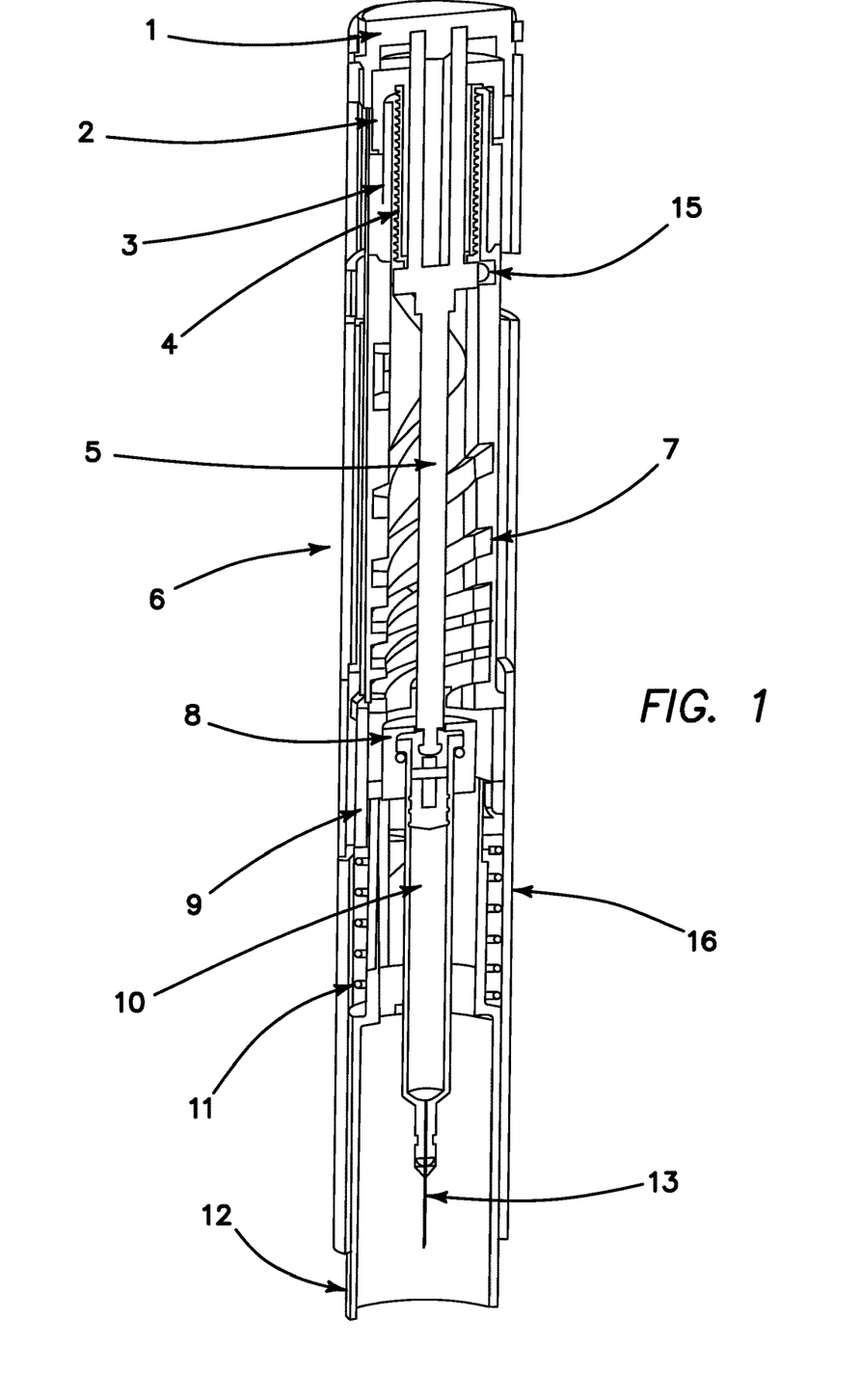
FIG. 1 is a cross-sectional schematic of the preferred autoinjector with the sleeve activation and needle lockout features installed.

In one preferred embodiment as described in the drawings, the autoinjector 6 may include an activation sleeve release and a needle lockout mechanism. Plunger screw 5 can be powered preferably by a combination torsion and compression spring 4, or by other types of springs. The distal end of plunger screw 5 is seated in the end cap 1 such that the plunger screw 5 is prevented from rotation.

Figure 2A:
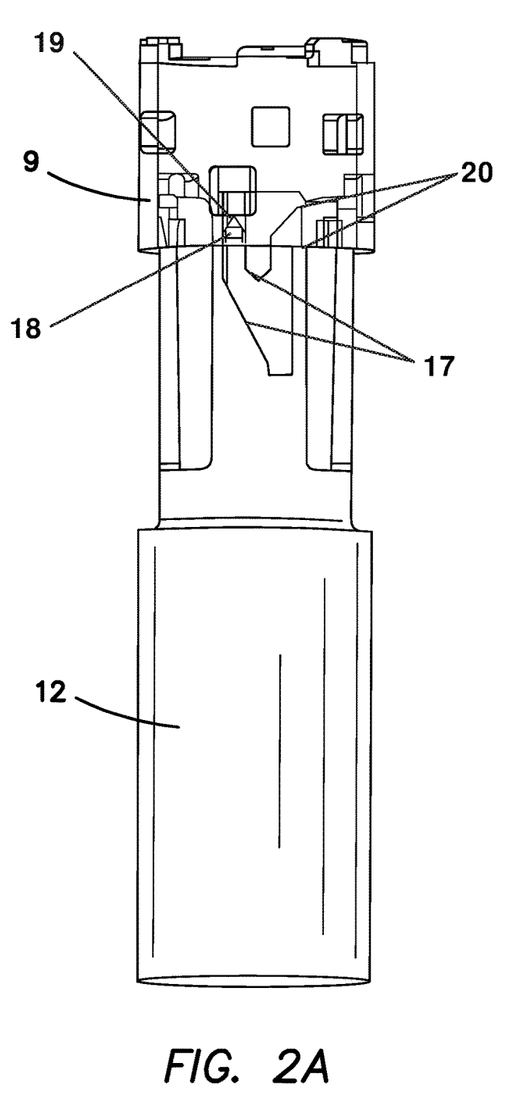
FIG. 2A is a close-up schematic view of the locking sleeve with the locking collar.
Figure 2B:
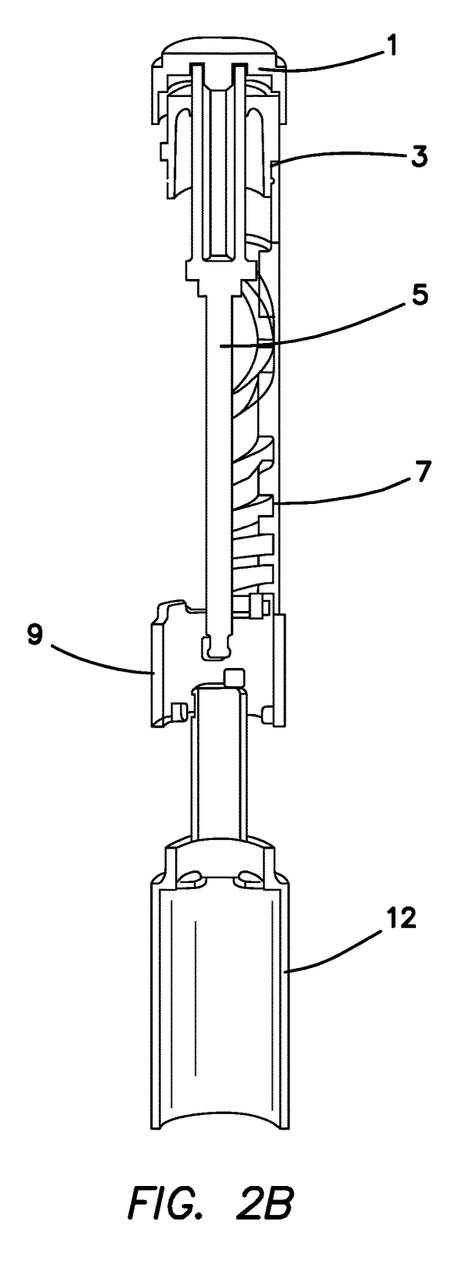
FIG. 2B is an isolated schematic view of the sleeve activation feature.

When the activation sleeve 12 is pressed against a surface (typically the skin of a human or non-human animal), ramp surfaces on the distal end of the activation sleeve 12 cause locking collar 9 to rotate. This, in turn, rotates the nut sectors 3, which are secured by nut cap 2. Pins 15 on the plunger screw 5 are supported by support ledges on the nut sectors 3; when the nut sectors 3 rotate, the plunger screw pins 15 fall off support ledges and the plunger screw 5 is free to move toward the proximal end propelled by the drive spring 4. The pins 15 are projections from the plunger screw 5 that ride on surfaces of the nut sector threads 7.

A spring 11 disposed about the narrower, distal end of the activation sleeve 12 is compressed during injection. The spring 11 applies a force that pushes the activation sleeve 12 in the proximal direction, which covers the needle 13 when the injector is not being pressed against the skin (or other surface). The sleeve activation feature begins the drug delivery cycle. To initiate the drug delivery cycle, the activation sleeve 12 is placed against the skin and pressed by the patient. As the spring 11 loaded activation sleeve 12 slides into housing 16, ramp surfaces on the activation sleeve 12 causes the locking collar 9 to rotate. This, in turn, causes locking collar 9 to rotate the nut sectors 3 while the endcap 1 keeps the plunger screw 5 from rotating. This action of the locking collar 9 releases the plunger screw 5 to translate in the proximal direction. Upon release, the plunger screw 5 disengages from end cap 1 and translates, using the energy from the drive spring 4 to advance proximally. The axial movement of the plunger screw 5 pushes fluid out of the syringe 10, which is secured by syringe clip 8. After injection is complete, the patient lifts the device from the injection site, which allows the sleeve 12 to extend and lock by rotating the locking collar 9.

Figure 3A:
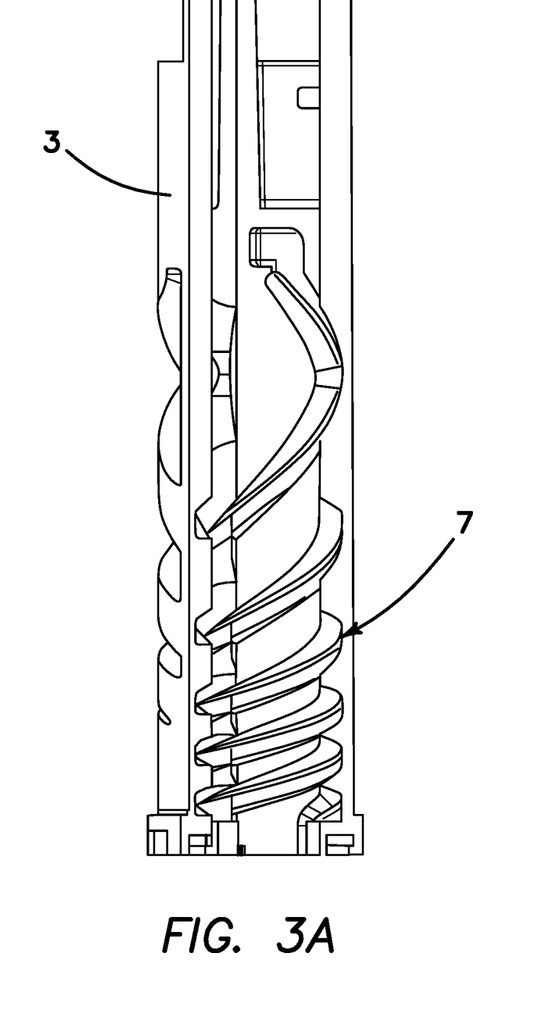
FIG. 3A is a schematic of the nut sectors without the EOD click feature.
Figure 3B:
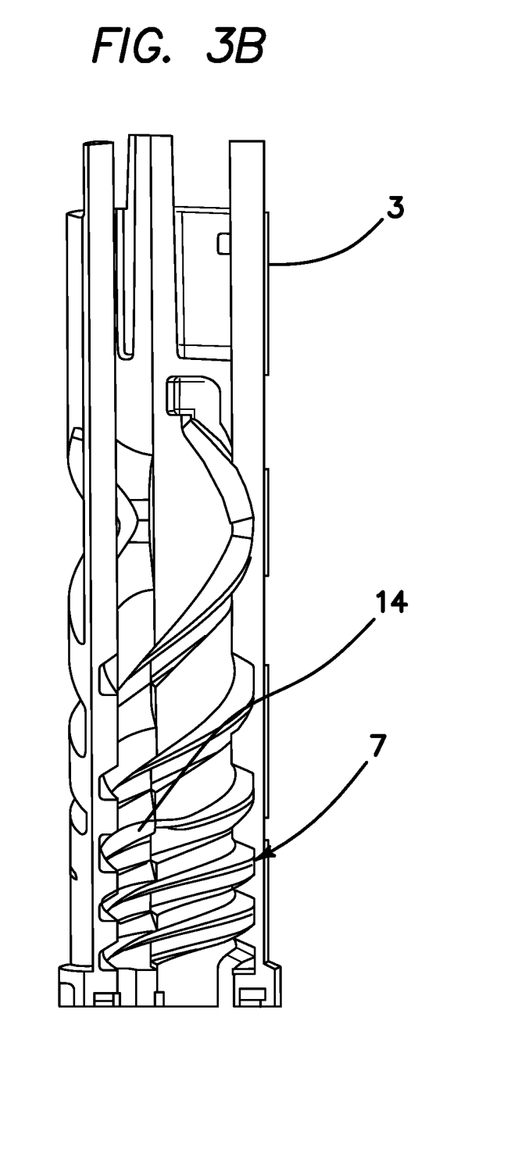
FIG. 3B is a schematic of the nut sectors with the EOD click feature.
Figure 4A:
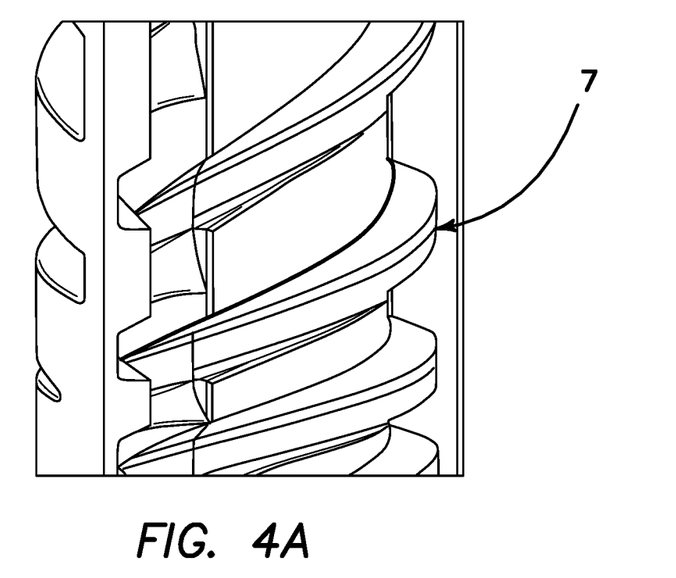
FIG. 4A is a close-up schematic view of the nut sector threads without the EOD click feature.
Figure 4B:
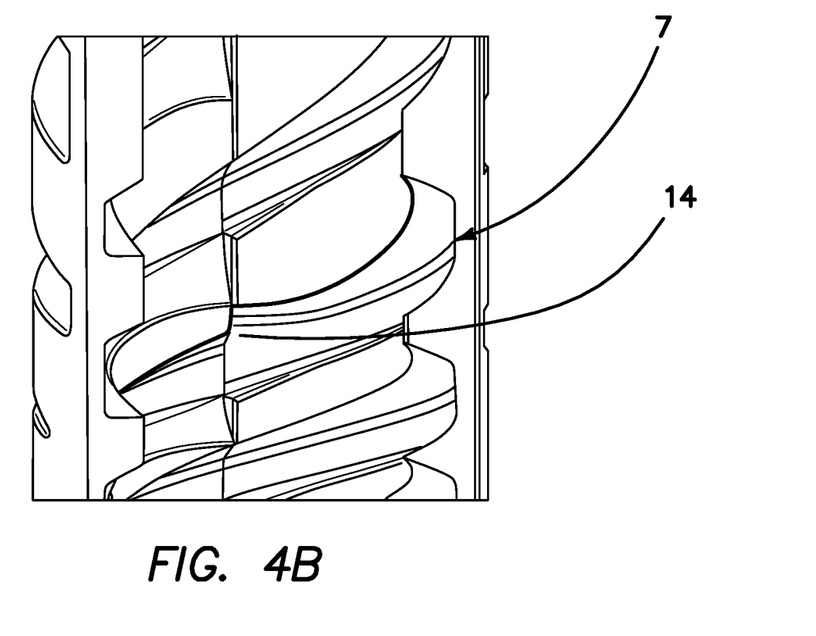
FIG. 4B is a close-up schematic view of the nut sector threads with the EOD click feature.

In another embodiment, the autoinjector may include an audible and tactile end-of-dose (EOD) indicator. The EOD indicator is a complement to the visual indicator of the plunger screw 5 in the syringe 10. An audible and tactile EOD indicator is in the form of a click sound and the small accompanying vibration associated with the sound. This feature provides audible and tactile feedback to the patient that the dose is complete, and the device can safely be removed from the skin. In a preferred embodiment of this feature, the helical nut sector threads 7 includes an abrupt interruption 14 in the rotational constraint they apply to the pins 15 on the plunger screw 5. A thread including at least one of these interruptions 14 can be called a "stepped" thread. When the plunger screw 5 rotates past this interruption 14, a click sound and a momentary light vibration are produced.

Figure 5:
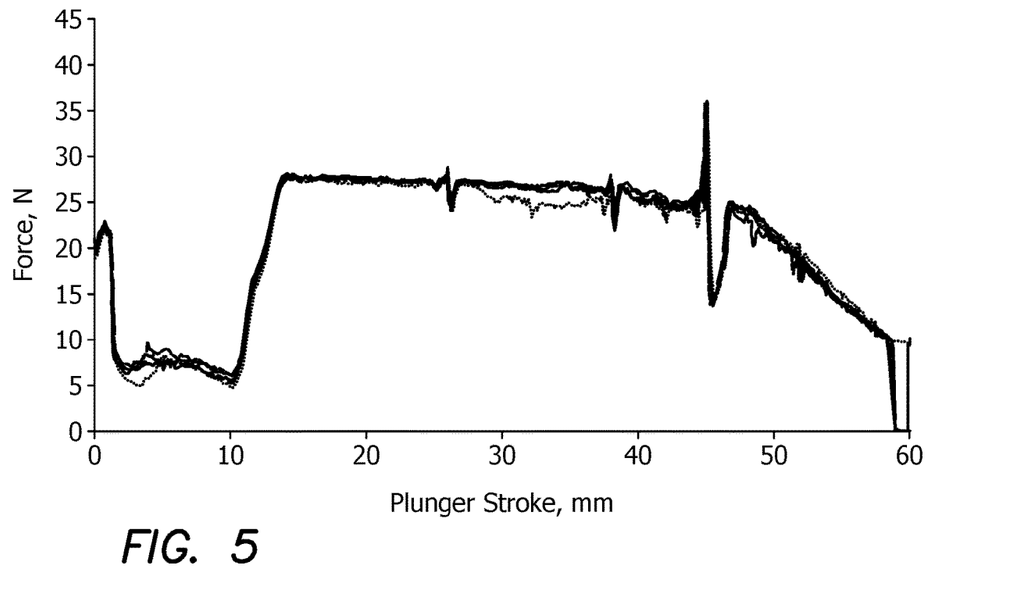
FIG. 5 is a plot of force applied to the plunger screw as a function of distance illustrating the change in force corresponding to a click sound.

FIG. 5 is a plot of force vs plunger motion of the invention with the EOD indicator. At the beginning of stroke, the needle insertion force ranges from 5 N to 10 N. During injection of the fluid medication for a syringe with a plunger stroke of up to 45 mm, the injection force from beginning to end of stroke ranges from 29 N to 24 N. The small spikes observed during stroke are due to seams within the threading of the nut sectors. The large spike at the end of the stroke is due to the EOD indicator feature. The force decline thereafter is an artifact of the mechanism "relaxing" in the test stand as the displacement head continues to move up and represents unused residual energy. The residual energy that exists after drug delivery could be used to drive post-drug delivery capabilities.

The results illustrated in FIG. 5 are for a particular device having a constant force of about 25 N; however, the invention is broadly applicable to a range of autoinjectors having various force profiles that can be selected according to the desired use. Depending on the desired use, the autoinjector can have a constant or a tailored force profile. Then this profile can be modified by insertion of a feature that causes a rapid change in force that results in an audible and/or tactile "click" that informs the user that the dose is ended or ending. The feature preferably causes a relatively fast increase, followed by rapid decrease in force on the plunger screw. The force on the plunger screw just prior to the interrupted motion (which is the constant force in a constant force injector, or the force just prior to the relatively fast increase in force in a non-constant force device) is termed the pre-click force. In some preferred embodiments, force on the plunger screw increases by at least 10% or at least 20%, or at least 25%, or in the range of 10 to 50%, and then reduces to the pre-click force or less over a distance in the proximal direction over a distance of 4 mm or less, 2 mm or less, or 1 mm or less (or in the range of 0.3 to 3 mm). This can be accomplished by a ramp on the surface of the thread upon which the pin rides; the slope of the ramp moves toward the distal direction. At the interruption, the pin(s) of the plunger screw undergoes a rapid change in motion corresponding to the rapid change in force applied to the plunger screw. Alternatively, a click can be produced by a step or step-like interruption without the ramp wherein force on the plunger screw decreases by at least 10% or at least 20%, or at least 25%, or in the range of 10 to 50%, over a distance in the proximal direction over a distance of 4 mm or less, 2 mm or less, or 1 mm or less (or in the range of 0.3 to 3 mm). After the decrease, the force may (or may not) return to the pre-click force over a distance of 4 mm or less, 2 mm or less, or 1 mm or less (or in the range of 0.3 to 3 mm).

In some preferred embodiments, the force on the plunger screw both increases and decreases (see, for example, the pattern shown in FIG. 5) over a distance of 4 mm or less, 2 mm or less, or 1 mm or less (or in the range of 0.5 to 4 mm or 0.5 to 3 mm).

Test Procedure

Figure 6:
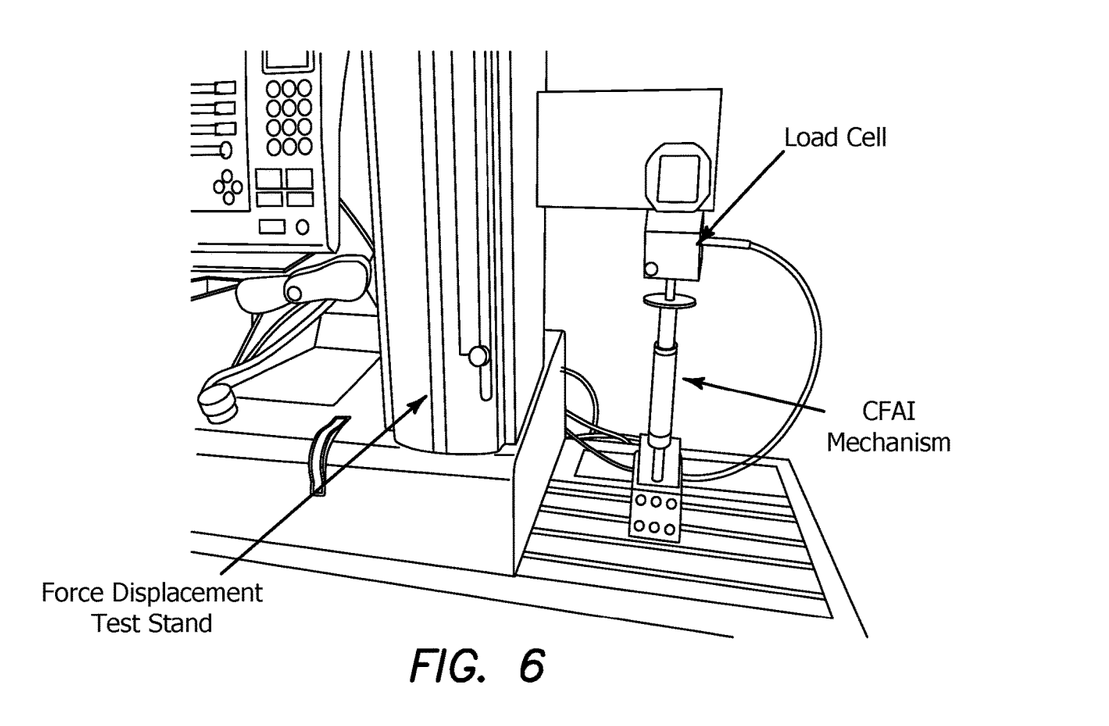
FIG. 6 is a drawing of the apparatus that was used to measure the force that is plotted in FIG. 5.

The injection force was measured at the end of the plunger screw using the Chatillon force measurement system apparatus shown in FIG. 6. This is a direct measurement of the injection force that the device applies to the plunger in the syringe to deliver the drug. The 25 N constant force auto-injector (CFAI) drive mechanism was set up in a force displacement test stand and released so that the tip of the plunger screw was sitting against the load cell. The Chatillon head moved upwards 60 mm at 200 mm/min while measuring the force exerted by the spring. The displacement head on the stand moved up at the controlled rate while the force exerted on the load cell was measured. The force vs displacement data is graphed to create the injection force profiles shown in FIG. 5. The large spike at the end of the graph is due to the end-of-dose click feature. The force decline thereafter (the relatively gradual decrease from 25 to ION) is an artifact of the mechanism "relaxing" in the test stand as the displacement head continues to move up. This happens after the working range of the mechanism and would not be seen in an actual device. Several devices were tested and results are superimposed as shown in FIG. 5.

What is claimed:

1. An autoinjector comprising:
    an activation sleeve which is rotationally keyed to a housing and is adapted to slide axially within the housing,
    a sleeve spring that applies an axial force between the housing and the activation sleeve;
    a locking collar that is secured axially and can rotate within the housing and is adapted to rotate as the activation sleeve is pushed or allowed to extend;
    nut sectors that are rotated by rotation of the locking collar and are captured axially between the locking collar and an end cap;
    a nut cap which secures the nut sectors and supports one end of a drive spring; and
    the end cap that engages with features on the housing and is locked to the housing with a cap lock.

2. The autoinjector of claim 1 further comprising a plunger screw with plunger screw pins that rests on nut sector shelfs and is rotationally keyed to the end cap, and provides a seat for the drive spring.

3. The autoinjector of claim 1 wherein the activation sleeve is used to activate the autoinjector.

4. The autoinjector of claim 1 wherein the activation sleeve is extended by the sleeve spring after use to cover the needle and preventing exposure of a needle.

5. The autoinjector of claim 1 wherein the locking collar is rotatable by the activation sleeve using ramped surfaces that interact with a cam feature in the locking collar.

6. The autoinjector of claim 1 wherein the activation sleeve is locked at the fullest extended position by the locking collar after use.

7. The autoinjector of claim 1 wherein the locking collar has features that interact with the activation sleeve to prevent the activation sleeve from moving axially after being extended to the fullest extended position after use.

8. The autoinjector of claim 1 wherein the nut sectors further comprise a stepped thread capable of producing an audible sound to provide audible feedback to the patient at an end of dose.

9. A method of protecting exposure to a needle on the autoinjector of claim 1 after an injection, comprising:
    providing the autoinjector wherein the injector comprises the activation sleeve that is located at a proximal end of the autoinjector and wherein the activation sleeve comprises the sleeve spring;
    applying a force to the activation sleeve from the sleeve spring to extend the activation sleeve when the autoinjector is removed from the skin surface of a patient; and
    rotating the locking collar near distal end of the activation sleeve extension causing locking tabs to interact with the activation sleeve causing the activation sleeve to lock in the extended position.

* * * * *